United States Patent [19]

Bauman

[11] Patent Number: 5,537,998
[45] Date of Patent: Jul. 23, 1996

[54] EMERGENCY MANUAL RESUSCITATOR WITH MEANS FOR DETECTING AIR PRESSURE

[76] Inventor: Jack Bauman, 2210 Wilshire Blvd., #705, Santa Monica, Calif. 90403

[21] Appl. No.: 276,411

[22] Filed: Jul. 18, 1994

Related U.S. Application Data

[63] Continuation-in-part of Ser. No. 276,614, Jun. 29, 1994, which is a continuation-in-part of Ser. No. 935,192, Aug. 26, 1992, abandoned, which is a continuation of Ser. No. 487,399, Mar. 20, 1990, Pat. No. 5,140,982, which is a continuation-in-part of Ser. No. 313,157, Feb. 21, 1989, Pat. No. 5,067,487, which is a continuation-in-part of Ser. No. 3,368, Jan. 14, 1987, abandoned, which is a continuation-in-part of Ser. No. 80,388, Jul. 31, 1987, Pat. No. 4,821,713.

[51] Int. Cl.[6] .................... A62B 9/00; A61M 16/00; G01L 7/00; F16K 21/00
[52] U.S. Cl. ................ 128/205.23; 128/205.13; 128/202.22; 137/557; 137/535; 73/700
[58] Field of Search .................. 128/202.22, 202.27, 128/205.23, 205.24, 725, 727, 728; 73/29.03, 29.04, 700, 715; 137/154, 455, 461, 488, 492.5, 505.11, 535, 538, 540, 557

[56] References Cited

U.S. PATENT DOCUMENTS

| | | |
|---|---|---|
| 2,399,643 | 5/1946 | Kreiselman . |
| 3,017,881 | 1/1962 | Smith . |
| 3,097,642 | 7/1963 | Russell . |
| 3,342,200 | 9/1967 | Wilcox . |
| 3,366,133 | 1/1968 | Johannisson . |
| 3,417,727 | 12/1968 | Nemes . |
| 3,435,839 | 4/1969 | Elder . |
| 3,473,529 | 10/1969 | Wallace . |
| 3,474,785 | 10/1969 | Jansson . |
| 3,530,857 | 9/1970 | Miczka . |
| 3,556,122 | 1/1971 | Laerdal . |
| 3,780,693 | 12/1973 | Parr . |
| 3,799,185 | 3/1974 | Milnes et al. . |
| 3,827,451 | 8/1974 | Roob . |
| 3,850,171 | 11/1974 | Ball et al. . |
| 3,882,860 | 5/1975 | Frimberger . |
| 3,949,610 | 4/1976 | Pietsch . |
| 4,016,885 | 4/1977 | Bruner . |
| 4,037,595 | 7/1977 | Elam . |
| 4,088,131 | 5/1972 | Elam et al. . |
| 4,098,296 | 7/1978 | Grasso et al. . |
| 4,106,502 | 8/1978 | Wilson . |
| 4,203,385 | 5/1980 | Mayer et al. . |
| 4,239,038 | 12/1980 | Holmes . |
| 4,249,527 | 2/1981 | Ko et al. . |
| 4,361,107 | 11/1982 | Gereg . |
| 4,374,521 | 2/1983 | Nelson et al. . |
| 4,444,201 | 4/1984 | Itoh . |

(List continued on next page.)

FOREIGN PATENT DOCUMENTS

| | | |
|---|---|---|
| 864140 | 4/1941 | France . |
| 1175514 | 8/1964 | Germany . |
| 1491631 | 4/1970 | Germany . |
| 2063687 | 6/1981 | United Kingdom . |
| 2145335 | 3/1985 | United Kingdom . |

*Primary Examiner*—Kimberly L. Asher
*Attorney, Agent, or Firm*—William W. Haefliger

[57] ABSTRACT

An elastomeric bag having opposite ends, a first opening at one of the bag ends and adapted to be connected to a resuscitator assembly, a second opening at the other of the bag ends, and a one-way flap valve at the second opening. The bag when compressed manually causes air to flow out through the first opening to the resuscitator assembly; and the bag, when allowed to expand, causes air to flow into the bag via the second opening past the one-way flap valve. A hollow plunger is slidably mounted within a cylinder bore, and a compressor spring biases the plunger. A post is located in the cylinder to seat one end of the spring, so that the spring urges the plunger toward the bag. An air vent is located in the cylinder and toward which the plunger is movable when the bag is compressed; and an air pressure release hole in the cylinder releases excess air pressure in the cylinder to the exterior, only after the plunger has been moved by air pressure to compress the spring to predetermined extent.

16 Claims, 5 Drawing Sheets

U.S. PATENT DOCUMENTS

| | | |
|---|---|---|
| 4,468,969 | 9/1984 | Schwartz . |
| 4,473,082 | 9/1984 | Gereg . |
| 4,499,846 | 2/1985 | Bergeron et al. . |
| 4,539,985 | 9/1985 | Magrath . |
| 4,669,415 | 6/1987 | Boord . |
| 4,821,713 | 4/1989 | Bauman . |
| 4,823,828 | 4/1989 | McGinnis . |
| 4,856,548 | 8/1989 | Paluch . |
| 4,898,165 | 2/1990 | Warzeka . |
| 5,067,487 | 11/1991 | Bauman . |
| 5,140,982 | 8/1992 | Bauman . |

EMERGENCY MANUAL RESUSCITATOR WITH MEANS FOR DETECTING AIR PRESSURE

This application is a continuation-in-part of Ser. No. 08/267,614 filed Jun. 29, 1994; which is a continuation-in-part of Ser. No. 07/935,192 filed Aug. 26, 1992 (abandoned); which is a continuation of Ser. No. 07/487,399 filed Mar. 20, 1990, now U.S. Pat. No. 5,140,982, issued Aug. 25, 1992; which is a continuation-in-part of Ser. No. 07/313,157 filed Feb. 21, 1989, now U.S. Pat. No. 5,067,487, issued Nov. 26, 1991; which is a continuation-in-part of Ser. No. 07/003,368 filed Jan. 14, 1987 (abandoned); which is a continuation-in-part of Ser. No. 07/80,388 filed Jul. 31, 1987, now U.S. Pat. No. 4,821,713 issued Apr. 18, 1989.

BACKGROUND OF THE INVENTION

This invention relates generally to resuscitation of newborn babies, or victims of respiratory or cardiac failure, as during heart attacks, shock, drowning, etc., and other conditions requiring Cardio-Pulmonary-Resuscitation (CPR). More particularly, it concerns an improved apparatus, characterized by high reliability, simplicity of construction, ease of use and safety against infection for rescuer and victim, and incorporation of multiple safety measures, including an integral manometer with a safety pressure release.

In the past, mouth-to-mouth resuscitation was used to provide the pulmonary portion of cardiopulmonary resuscitation (CPR), but the risk of infection to rescuers has caused many to refuse to perform this procedure. There is need for a simple, safe, and inexpensive manual resuscitation apparatus that is easy to use.

SUMMARY OF THE INVENTION

It is a major object of the invention to provide apparatus meeting the above need. Basically, the resuscitation apparatus of the invention comprises:

a) an elastomeric bag with an open port in one end (to be connected to a resuscitator assembly), and a one-way flap valve in its opposite end; wherey, when the bag is compressed manually, air flows out of the resuscitator port into the resuscitator assembly; and when the compressed bag is allowed to re-expand, air flows in through the one-way flap valve, refilling the bag with air (or oxygen), b) a transparent cylinder having a cylindrical bore with a first port means for attachment to the elastomeric bag, c) a flat flap valve located in the cylinder to allow air to flow only in the direction away from the bag, d) an exhalation port and channel in the cylinder, and which is closed by the above flap valve when air flows from the bag, and which is opened when exhaled air flows from the patient, e) a second port means in the side of the cylinder, at right angles to its long axis, for attachment to the patient's face mask or endotracheal tube, f) a hollow plunger slidably mounted within the bore, the plunger biased by a compression spring, g) a post which resists movement of the compression spring, the post carried by the cylinder, h) an air vent toward which the plunger is movable when the bag is compressed, i) and a hole in the bore wall to release excess gas pressure to the exterior, only after the plunger has compressed the spring to a predetermined extent.

Another object of the invention is to provide a low cost transparent cylindrical wall means for such apparatus with indicia above the slidable plunger, to indicate air pressure within the resuscitator assembly (and therefore the patient's lungs).

The pressure-detecting device portion of the invention may be incorporated into the passage structure of the resuscitator (integral with the resuscitator), or it may be constructed for attachment to resuscitators that have no pressure-detecting mechanism, i.e., as auxiliary attachment equipment.

Another object is to provide for adjustment of excess pressure level released, by use of an adjustable means with multiple apertures, as in the form of a rotatable sleeve.

Yet another object is to provide a plunger defining a recess into which the post projects, the spring also located in the recess. In addition, the plunger may be provided with an end surface facing the passage means, and the plunger has a side wall blanking an air release port means until the plunger moves to register its end surface with the port.

An additional object is to form a first port through the wall means, and to provide a second port through the wall means and spaced from the first port to pass excess fluid pressure when the first port is blanked.

The device of the invention may be constructed for attachment to a resuscitator apparatus passage means at the exterior of associated wall means, i.e., as auxiliary attachment equipment; or it may be incorporated into the passage means structure of the resuscitator.

Another object is to provide for adjustment of the excess pressure level released by use of an adjustable means with multiple apertures, as in the form of a rotatable and apertured sleeve.

These and other objects and advantages of the invention, as well as the details of an illustrative embodiment, will be more fully understood from the following specification and drawings, in which:

DETAILED DESCRIPTION

Figure 1:
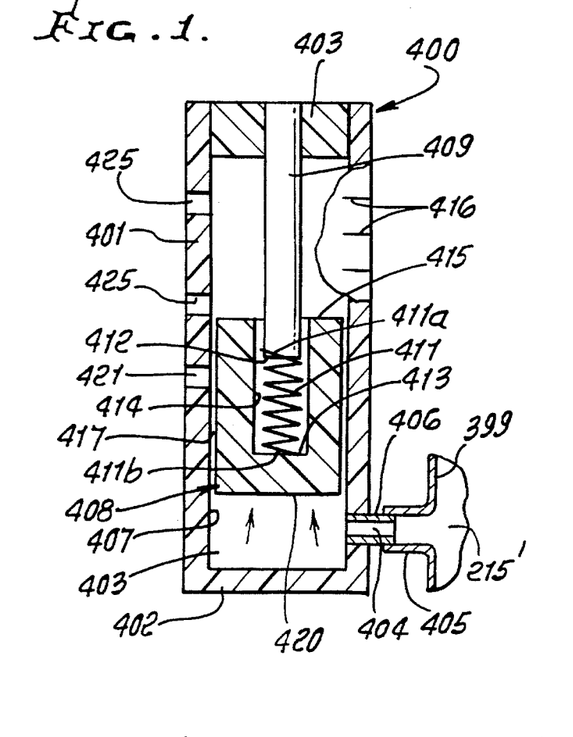
FIG. 1 is a section taken through a pressure release device which can be attached as an accessory to other breathing devices or resuscitators.

Referring to FIG. 1, it includes a cylindrical body 400 having a cylindrical wall means 401, closed at one end by wall 402. Wall means 401 may be transparent and formed of plastic material. A plug 403 closes the opposite end of the body. An inlet port 404 near wall 402 is adapted to pass air into the body passage means 403, as from a resuscitator structure passage indicated at 215'. Slide on attachment to the resuscitator is provided by telescopic tubes 405 and 406. Breathing mechanism is indicated at 399, and may incorporate structure, as disclosed in any of the applications of which this is a continuation, such applications incorporated herein by reference.

A cylindrical bore 407 is formed by body 400, and a plunger 408 is slidably mounted to, i.e., in the bore. A post 409 extends centrally in the body toward the plunger, from a plug 403, acting to seal or close the cylindrical body at its opposite end. A spring means is mounted intermediate the post and the plunger. Specifically, a coil spring 411 has one end 411a seated on the end 412 of the post, and its opposite end 411b seated against an interior end wall 413 defined by the plunger, internally of an axial recess 414 formed in the plunger. Spring 411 yieldably resists upward or endwise displacement of the plunger toward the post.

Plunger upper end or edge 415 variably registers with pressure indicating indicia lines 416 formed on the wall 401, as the plunger moves endwise in response to air pressure communicated to passage means 403. Plunger end 415 can be viewed when wall 401 is transparent. The plunger may have a distinctive color.

The cylindrical plunger fits closely to bore 407, but some clearance 417 is provided therebetween. If the air pressure reaches an upper, safe limit, the plunger moves upward so that its lower end surface 420 comes into registration with a through hole or port 421 in side wall 401, whereby air escapes and the pressure in the passage 403 and in the resuscitator passage 415' is limited to a safe upper level (as respects the patient's lungs). A second through hole or vent port 425 is located in wall 403 to allow venting of air pressure above the plunger, as the plunger moves upwardly in response to pressure increase below the plunger.

FIGS. 2–5 show a modified, selective, pressure release system associated with the basic device or apparatus, as shown in FIG. 1. That apparatus remains the same, as seen in FIG. 1, except that there are first and second through holes 421 and 442 in the cylindrical wall means 401; and, preferably, there is also a third such hole 443 in the wall means. The holes are separated in the direction of plunger movement, as for example in the direction of axis 444.

Figure 2:
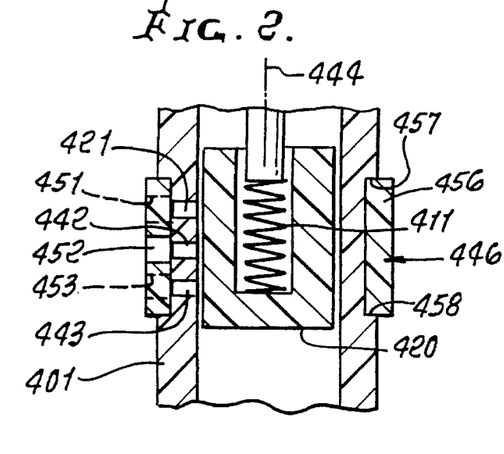
FIG. 2 is a view like FIG. 1 showing a modification.

Sleeve means 446 is provided adjacent the wall means and defines first and second through aperture means, as at 451 and 452; and, preferably, there is a third such aperture 453 in the sleeve. These apertures are formed in the wall 456 of the sleeve 446 to selectively register with the holes 421, 442 and 443 as the sleeve is rotated relative to wall 401. The sleeve is shown as cylindrical to closely fit the cylindrical wall 401; and support shoulders 457 and 458 on wall 401 engage opposite ends of the sleeve to locate the sleeve axially on the cylindrical wall 401 and to provide slight friction so that the sleeve will remain in a selected, rotated position.

The user can select one of three different excess air pressure levels (in bore 403 and resuscitator passage 215') at which the excess pressure is released to the exterior. Sleeve means 446 is rotated to achieve this selection.

Figure 3:
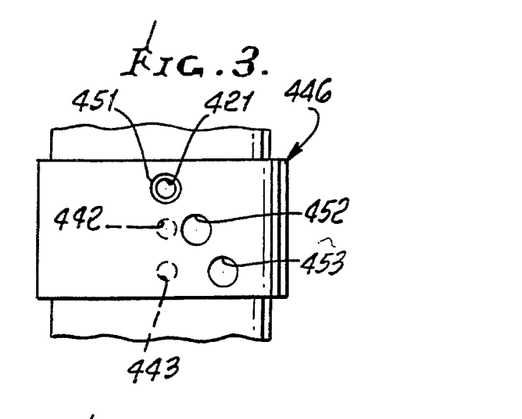
FIGS. 3–5 are side views of devices, as in FIG. 2, and showing aperture sleeve positions.

In sleeve FIG. 3 position, sleeve 446 has been rotated about axis 444 to cause aperture 451 to register with hole 421, the uppermost hole in FIG. 2. Accordingly, the underside 420 of the plunger must rise to level of hole 421 to release excess pressure $P_1$ in chamber 403 and resuscitator passage 215' (see FIG. 1). The spring 411 must be compressed to a higher force level to permit such pressure release. Holes 442 and 443 are blanked by the sleeve.

Figure 4:
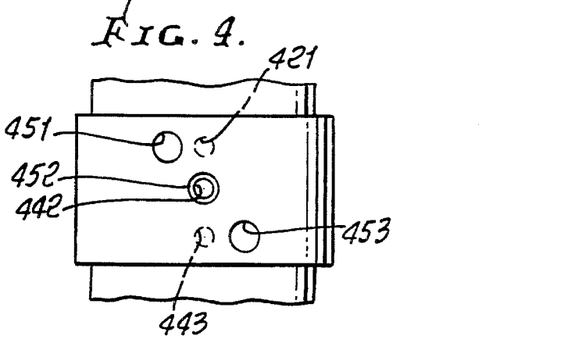

In sleeve FIG. 4 rotated position, aperture 452 has been rotated with the sleeve into registration with hole 442 in wall means 401, allowing air pressure release at a medium pressure level $P_2$. Holes 421 and 443 are blanked by the sleeve.

Figure 5:
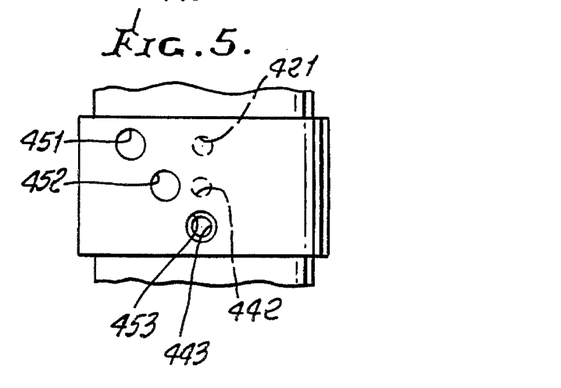
Figure 6:
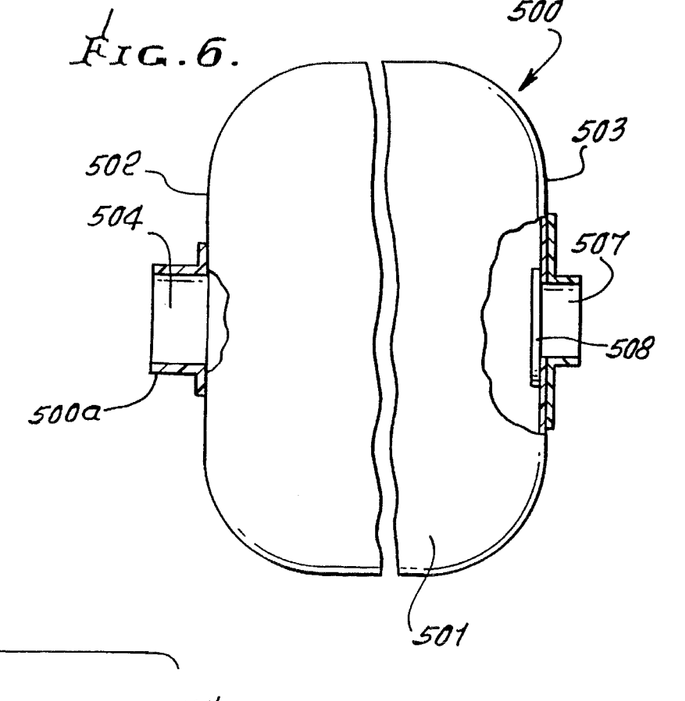
FIG. 6 shows the elastomeric self-expanding, manually compressible air bag with inlet and outlet ports.
Figure 7:
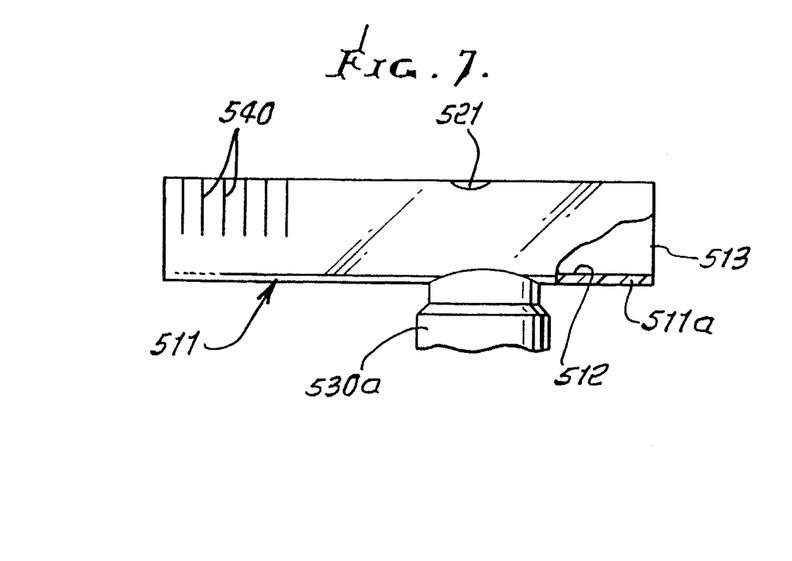
FIG. 7 is a perspective view of the transparent hollow cylinder into which resuscitator components are mounted.
Figure 8:
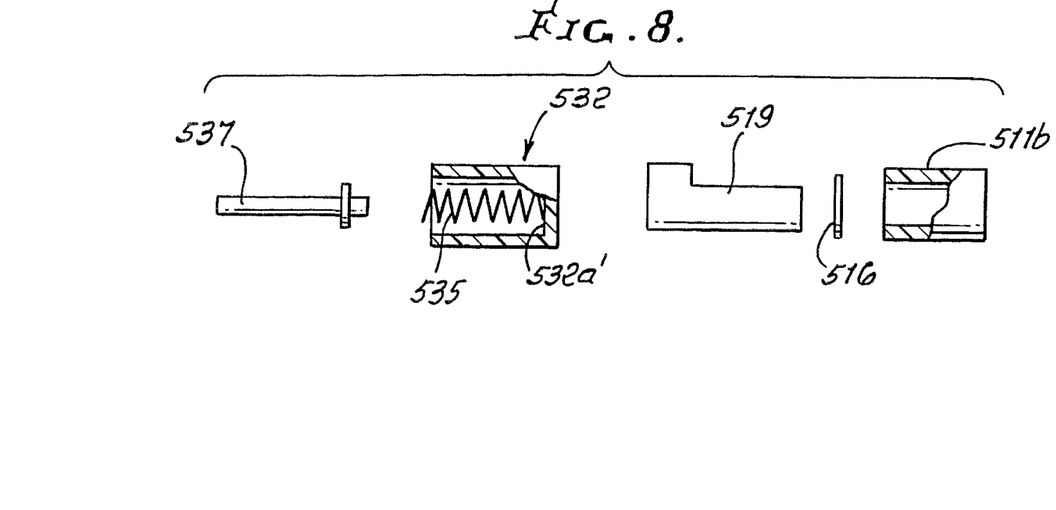
FIG. 8 shows the internal components in an exploded view.

In FIG. 5, the sleeve has been rotated to bring aperture 453 into registration with hole 443 in the wall 401, allowing air pressure release at a lower level $P_3$. Holes 421 and 442 are then blanked by the sleeve. In this regard, $P_1>P_2>P_3$.

Note that apertures 451, 452, and 453 are offset relative to one another in either direction of sleeve means rotation.

Summarizing operations in FIGS. 1–5:

i) when the sleeve means is adjusted to a first position relative to the wall means, the first aperture means registers with the first hole to thereby release excess gas pressure in response to spring means compression by the plunger to first predetermined extent, and at which time the second and third holes are blanked by the sleeve means;

ii) when the sleeve means is adjusted to a second position relative to the wall means, the second aperture means registers with the second hole to thereby release excess gas pressure in response to spring means compression by the plunger to second predetermined extent, and at which time the first and third holes are blanked by the sleeve means;

iii) and when the sleeve means is adjusted to a third position relative to the wall means, the third aperture means registers with the third hole to thereby release excess gas pressure in response to spring means compression by the plunger to a third predetermined extent, and at which time the first and second holes are blanked by the sleeve means.

Plungers, as disclosed herein, can be made of NYLON, or TEFLON (tetrafluoroethylene), or DELRIN, for example, to have lubricity or slidability. There should be minimal clearance between the plunger and its surrounding cylindrical wall, as in FIG. 1.

Referring now to FIGS. 6–11, an elastomeric bag 500 comprises a thin elastomeric wall or shell 501 containing air or other gas, such as oxygen. The bag has opposite end walls 502 and 503. A first opening 504 is provided at one end 502 of the bag and is adapted to be connected to a resuscitator assembly, indicated generally at 506. A second opening 507 is provided at the other end 503; and a one-way flap valve 508 is provided at the second opening. The construction is such that, when the bag is yieldably resiliently manually compressed (see in FIG. 10 force arrows $F_1$ and $F_2$), flap valve 508 closes and air within the bag is caused to flow out through the first opening 504 (see flow arrow 505), to the resuscitator assembly 506; and, when the bag is allowed to expand resiliently outwardly, air is caused to flow into the bag via the second opening 507 and past the flap valve 508 opened by such flow. See flow arrow 509 in FIG. 11.

The assembly 506 includes a transparent plastic (or glass) cylinder 511 having a cylindrical bore 512. It also has a first port 513 at its end closest to the bag opening 504. Cylinder end wall 511a may have telescopic connection to the tubular end 500a of the bag, via couplings 511b, 511c and 511d. Port 513 directly communicates with opening 504, to receive bag air flow.

A second flap or disc valve 516 is located in the cylinder 511 to allow bag air to flow around or past that valve only in a direction (leftwardly in FIG. 10) away from the bag.

Such flow tends to open the flap valve leftwardly, to seat at 518 against the rightward end of insert tubular structure 519 in the cylinder. See flow arrows 520 in FIG. 10 leading toward a patient.

An air exhalation exit port 521, formed by structure 519, is effectively closed when flap valve 516 closes the rightward end of a channel 522 in insert structure 519, channel 522 leading to port 521.

Figure 11:
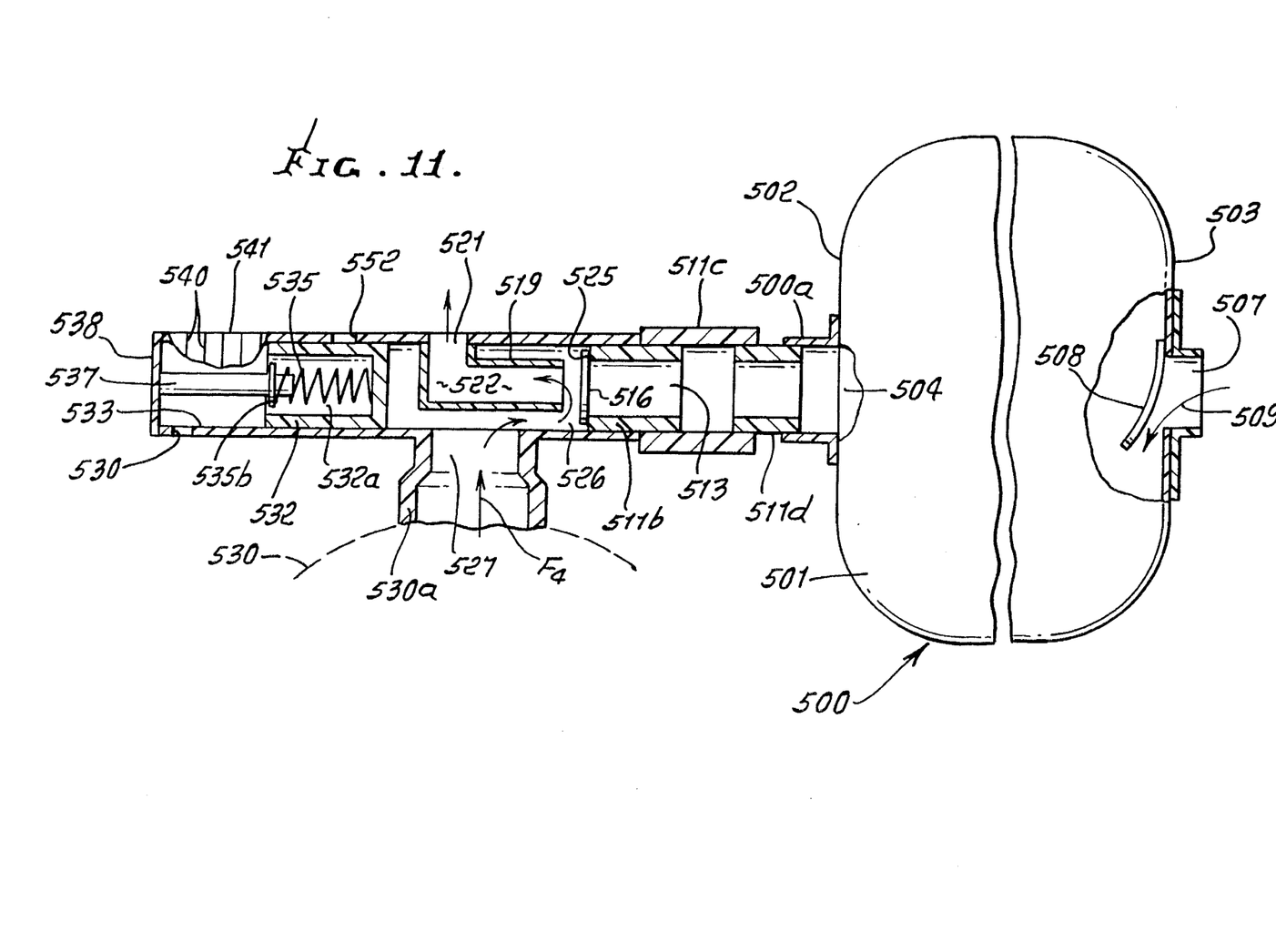
FIG. 11 shows the resuscitator during patient lung exhalation.

Flap valve 516 is opened, i.e., rightwardly displaced, to seat against the end 525 of an annular channel 526 in the cylinder, as seen in FIG. 11. This closes off communication between the bag interior and the interior of the cylinder at 527 in FIG. 11, and opens a path for exhalation air to flow away from the patient, to interior 527, then into channel 522 and to the exhalation port 521. See flow arrows $F_4$ in FIG. 11. Second port 527 is formed in the side wall of the cylinder, to communicate with a patient's face mask or endotracheal tube, indicated schematically at 530 in FIG. 11, as via a side duct 530a.

Figure 9:
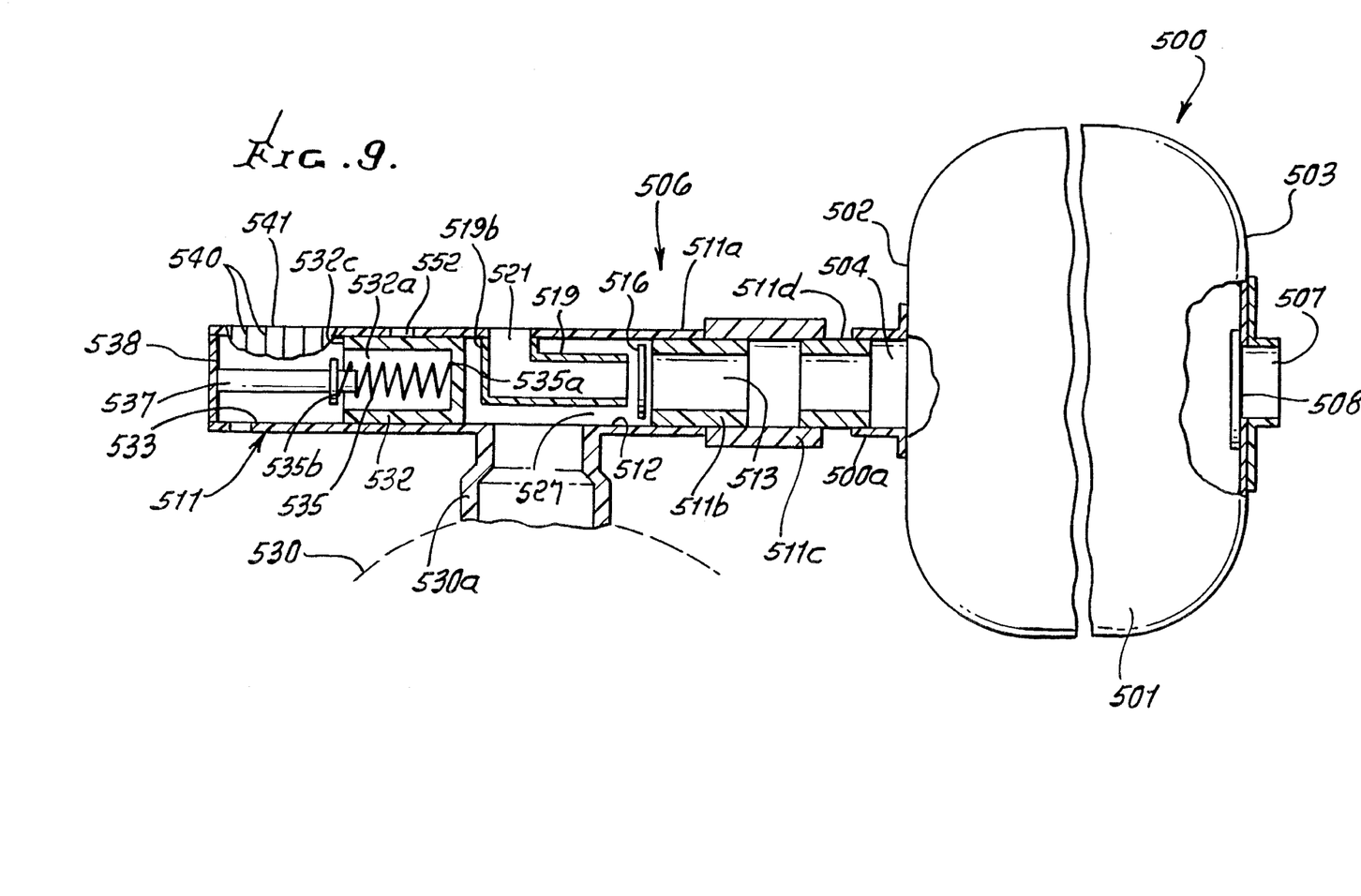
FIG. 9 shows the assembled components in their static position.
Figure 10:
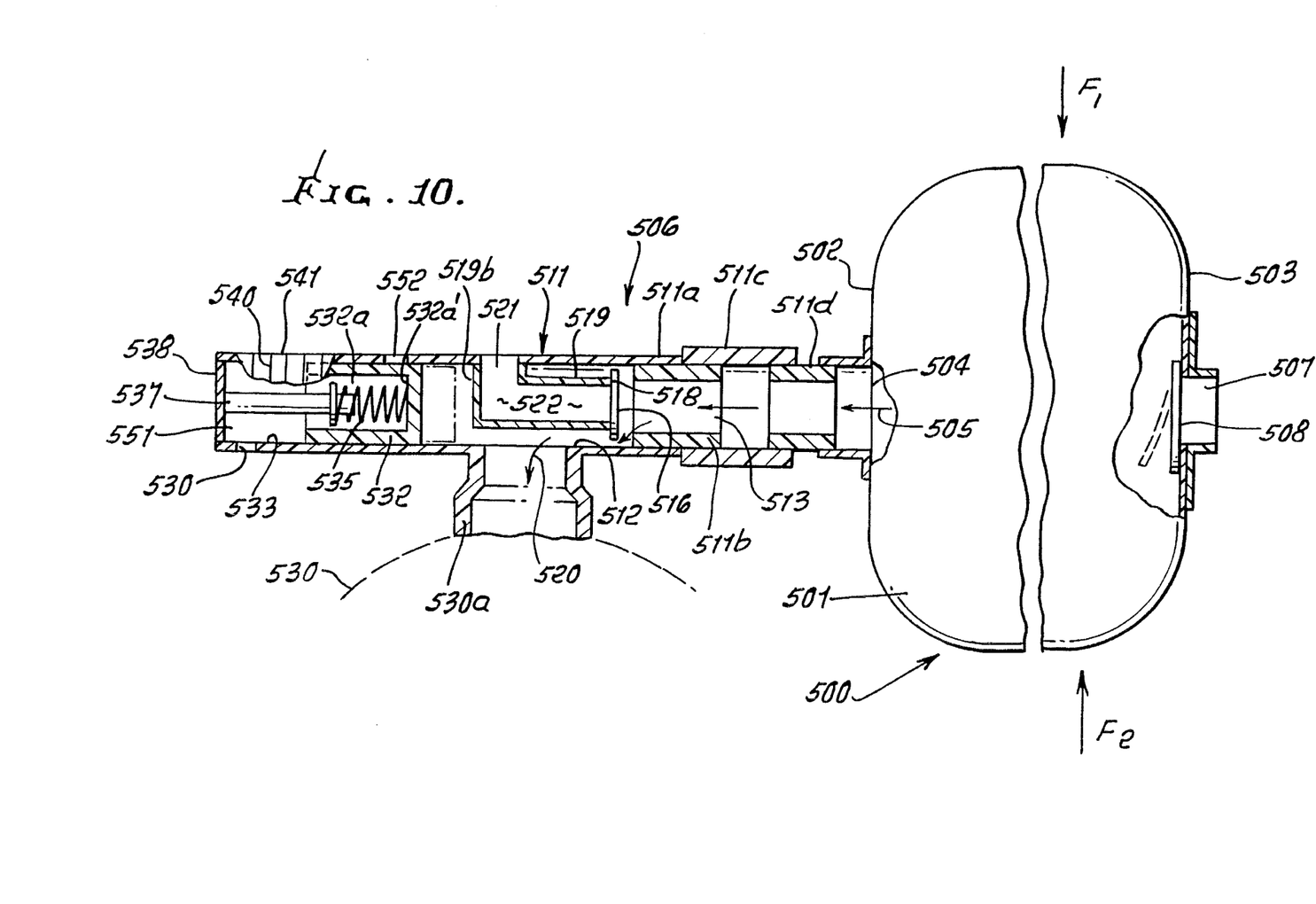
FIG. 10 shows the assembled resuscitator during patient lung inflation.

A hollow plunger 532 is slidably mounted or received in the cylinder bore 533 to slide axially in that bore (left and right in FIGS. 9–11). A compression spring 535 is received in the plunger hollow 532a and tends to urge the plunger to the right, i.e., toward the structure 519, which seats the plunger, as at 519b. See spring end 535a engaging plunger end wall 532a. A post 537 is located in the cylinder and carried by a plug 538 attached to the cylinder, as shown. The post extends into the plunger and engages or seats the left end 535b of the spring. Thus, the spring is compressed against the post, as the plunger is urged leftwardly by increasing air pressure in cylinder interior 527.

Spaced apart indicia lines 540 on the wall portion 541 of the cylinder successively register with the end 532c of the plunger, as the plunger moves to the left in FIG. 10, to indicate (by calibration) the degree of air pressure in the cylinder interior 527 and communicated to the patient's, i.e., baby's lungs. The plunger may have a distinctive color, such as yellow, for visibility through the cylinder transparent wall. Manometer function is thereby provided at a location very near the operator's hand manipulating the bag 500, and near the patient's face mask. This avoids the problem of employing a remote manometer requiring movement of the operator's head back and forth, while using a resuscitator and a remote manometer. An air vent 550 in the cylinder, and toward which the plunger moves leftwardly, passes air trapped in cylinder space 551.

An air pressure release hole 552 is provided in the cylinder wall, to release excess air pressure in space 527 to the exterior, only after the plunger has been moved by such air pressure to clear (move past) the hole 552, compressing the spring to predetermined extent. This prevents excess air pressure caused damage to the baby's lungs. A succession of such holes may be provided, as described in FIGS. 1–5, for selection of the level of air pressure to be allowed to exist in space 527 (i.e., higher pressure for adults, lower pressure for small children and infants).

I claim:

1. Apparatus for use in measuring breathing gas pressure in breathing mechanism having a passage means, and for safely releasing excess gas pressure, comprising in combination:

a) said apparatus including wall means defining a bore, said apparatus defining a first port means for communicating with said passage means to communicate gas pressure therein to said bore, b) a plunger slidably mounted in said bore, and a post extending within said bore, c) spring means mounted intermediate said post and said plunger so as to yieldably resist movement of the plunger relative to such wall means of said apparatus, d) and including a first hole in said wall means to release excess gas pressure in said passage means to the exterior, only after the plunger has compressed the spring means to first predetermined extent, thereby communicating said passage means with said first hole, said wall means defining a cylinder, e) and including a second hole in said wall means to release excess gas pressure in said passage means to the exterior, only after the plunger has compressed the spring means to second predetermined extent, there being sleeve means adjacent said wall means and defining first and second aperture means, and i) when the sleeve means is adjusted to a first position relative to said wall means, said first aperture means registers with the first hole to thereby release excess gas pressure in response to spring means compression by the plunger to said first predetermined extent, and at which time the second hole is blanked by the sleeve means, and ii) when the sleeve means is adjusted to a second position relative to the wall means, said second aperture means registers with the second hole to thereby release excess gas pressure in response to spring means compression by the plunger to said second predetermined extent, and at which time the first hole is blanked by the sleeve means.

2. The combination of claim 1 wherein said wall means is transparent.

3. The combination of claim 1 wherein said plunger defines a recess into which said post projects, said spring means located in said recess.

4. The combination of claim 1 wherein said plunger has an end surface facing said passage means, and said plunger has a side wall blanking said first hole until the plunger moves to register said end surface with said first hole.

5. The combination of claim 1 wherein said first hole is formed through said wall means, and including a second hole through said wall means and spaced from said plunger to allow gas to vent in spaced relation to the plunger.

6. The combination of claim 1 including said breathing mechanism carrying said apparatus.

7. The combination of claim 6 wherein said mechanism comprises a resuscitator.

8. The combination of claim 1 including means on the wall means supporting the sleeve means for rotation relative to the wall means.

9. Apparatus for use in measuring breathing gas pressure in breathing mechanism having a passage means, and for safely releasing excess gas pressure, comprising in combination:

a) said apparatus including wall means defining a bore, said apparatus defining a first port means for communicating with said passage means to communicate gas pressure therein to said bore, b) a plunger slidably mounted in said bore, and a post extending within said bore, c) spring means mounted intermediate said post and said plunger so as to yieldably resist movement of the plunger relative to such wall means of said apparatus, d) and including a first hole in said wall means to release excess gas pressure in said passage means to the exterior, only after the plunger has compressed the spring means to first predetermined extent, thereby communicating said passage means with said first hole, said wall means defining a cylinder, e) and including a second hole in said wall means to release excess gas pressure in said passage means to the exterior, only after the plunger has compressed the spring means to second predetermined extent, there being sleeve means adjacent said wall means and defining first and second aperture means, and i) when the sleeve means is adjusted to a first position relative to said wall means, said first aperture means registers with the first hole to thereby release excess gas pressure in response to spring means compression by the plunger to said first predetermined extent, and at which time the second hole is blanked by the sleeve means, and ii) when the sleeve means is adjusted to a second position relative to the wall means, said second aperture means registers with the second hole to thereby release excess gas pressure in response to spring means compression by the plunger to said second predetermined extent, and at which time the first hole is blanked by the sleeve means, f) and including a third hole in said wall means to release excess gas pressure in said passage means to the exterior, only after the plunger has compressed the spring means to third predetermined extent, said sleeve means also defining third aperture means, and iii) when the sleeve means is adjusted to a third position relative to said wall means, said third aperture means registers with the third hole to thereby release excess gas pressure in response to spring means compression by the plunger to a third predetermined extent, and at which time the first and second holes are blanked by the sleeve means.

10. The combination of claim 9 wherein said wall means defines a tubular bore, and said plunger is cylindrical to slide in said bore.

11. The combination of claim 10 wherein the cylinder is transparent.

12. The combination of claim 10 wherein the plunger has a distinctive color, and the cylinder is transparent.

13. The combination of claim 10 including indicia on the cylinder and toward which the plunger is movable to indicate the position of the plunger relative to the indicia, thereby to indicate the degree of air pressure in the cylinder.

14. The combination of claim 10 including a plug sealing said tubular bore and carrying said post.

15. The combination of claim 10 wherein said plunger has a distinctive color, and said wall means is transparent.

16. The combination of claim 9 wherein said sleeve means is rotatable relative to said wall means, and said first, second and third apertures are offset relative to one another in the direction of sleeve means rotation.

* * * * *